United States Patent [19]
Volk et al.

[11] Patent Number: 4,806,641
[45] Date of Patent: Feb. 21, 1989

[54] SALTS OF 3-HYDROXY-4-OXO-3,4-DIHYDRO-1,2,3-BENZOTRIAZINE AND AMINO COMPOUNDS

[75] Inventors: Alexander Volk, Eppstein/Taunus; Wolfgang König, Hofheim am Taunus, both of Fed. Rep. of Germany

[73] Assignee: Hoechst Aktiengesellschaft, Frankfurt am Main, Fed. Rep. of Germany

[21] Appl. No.: 741,866

[22] Filed: Jun. 6, 1985

[30] Foreign Application Priority Data

Jun. 8, 1984 [DE]  Fed. Rep. of Germany ....... 3421303

[51] Int. Cl.[4] ...................... C07D 253/08; C07K 5/06; C07K 5/08
[52] U.S. Cl. ..................................... 544/183; 530/331
[58] Field of Search ................. 544/183; 260/112.5 R, 260/998.2; 530/331

[56]  References Cited
  FOREIGN PATENT DOCUMENTS 2905502  9/1980  Fed. Rep. of Germany .
3117985  11/1982  Fed. Rep. of Germany .

OTHER PUBLICATIONS

Lu et al, Chem. Abstr., 95 (1981), 62784d.
Teetz et al, Chem. Abstr., 88 (1978), 105748v.
Ahern et al, Chem. Abstr., 88 (1978), 22841u.
Hardy et al, Chem. Abstr., 98 (1983), 17031g.
Lu et al, Chem. Abstr., 96 (1982), 100111n.
Chem. Abstr., 73 (1970), 56423q and 56424r.
*Perspectives in Peptide Chemistry*, Eberle et al. (Editors), S. Karger, 1981, pp. 15-30 and 143-149.
Chem. Ber., 103 (1970), 2034-2040.
Chem. Ber., 103 (1970), 2024-2033.
Brunfeldt, Peptides 1980, Copenhagen 1981, S. 174-179.
Benolton et al, Int. J. Peptide Protein Res., 17 (1981), 197-204.
Houben-Weyl, Methoden der Organischen Chemie, vols. XV/1 and XV/2.
Schroder et al., The Peptides, vol. 1, pp. 3-51, 1965.

*Primary Examiner*—John M. Ford
*Attorney, Agent, or Firm*—Finnegan, Henderson, Farabow, Garrett & Dunner

[57]  ABSTRACT

The invention relates to salts of 3-hydroxy-4-oxo-3,4-dihydro-1,2,3-benzotriazine (HOObt) and compounds containing a primary amino group, a process for their preparation and their use.

8 Claims, No Drawings

SALTS OF 3-HYDROXY-4-OXO-3,4-DIHYDRO-1,2,3-BENZO-TRIAZINE AND AMINO COMPOUNDS

Amines are usually isolated and purified in the form of their salts. In general, hydrochlorides and tosylates are prepared as well as, for example, picrates of bases which are difficult to crystallize. If these salts are to be acylated or alkylated, the bases must be freed from these salts again. This problem is usually solved for example by the addition of bases, such as tertiary amines, to the reaction mixture. These bases often introduce other impurities into the mixtures, must then be removed again and can lead to by-products. Salts with 1-hydroxybenzotriazole (HOBt) do not have these disadvantages (Int. J. Peptide Protein Res. 20, 387–395 (1982)) because these salts react with activated esters or with carboxylic acids, with the addition of dicyclohexylcarbodiimide (DCC), to give the corresponding amides. This also utilizes the catalytic effect of the HOBt, which accelerates the acylation of the amines with active esters (Chem. Ber. 106, 3626–3635 (1973)) and reduces the racemization in peptide synthesis using DCC (Chem. Ber. 103, 788–798 (1970)).

Now, there are a number of amines, for example L-threoninol or L-leucinol, which are difficult to purify. Thus, threoninol is prepared from threonine methyl ester and leucinol from leucine with reducing agents such as $LiAlH_4$. In these reactions, the amines are obtained as impure oils which could not be purified via the usual salts. Even with HOBt, these amines do not give crystallizing salts.

Surprisingly, these bases do crystallize with 3-hydroxy-4-oxo-3,4-dihydro-1,2,3-benzotriazine (HOObt). In this way, the bases can easily be isolated from mixtures and purified. Other amino compounds, for example amino acid esters, can also be purified by this method. Curiously, some of the amino compounds used, for example threoninol, crystallize only with two equivalents of HOObt. By contrast, other amino compounds, for example leucinol or H—Ser($Bu^t$)—$OBu^t$, only need one mol equivalent of HOObt. Amorphous HOObt salts, which can also be used for purifying bases, usually have a varying content of HOObt (between 1 and 2 mol equivalents).

The invention thus relates to salts of 3-hydroxy-4-oxo-3,4-dihydro-1,2,3-benzotriazine (HOObt) and compounds containing a primary amino group. These salts can be in the form of crystalline or amophous solids. The molar ratio HOObt:monoamino compound is preferably 1 to 2. The ratio is correspondingly greater in the case of diamino and polyamino compounds.

A compound containing a primary amino group (here called an amino compound) is understood in this context as being an acyclic, isocyclic or heterocyclic compound containing one or more primary amino groups and optionally one or more other functional groups, preferably of neutral character, in the molecule. Acid or basic groups, for example —COOH, —$SO_3H$ or —$N(CH_3)_3$, are less preferable.

The amino compound can be a primary amine such as a primary aliphatic amine (for example an alkylamine). It can additionally have a hydroxyl group or an ester group. It can be a derivative (for example an ester) or a modified form (for example the reduced form) of an α-amino acid or of a peptide. Appropriate naturally occurring α-amino acids are described, for example, in Houben-Weyl, Methoden der Organischen Chemie (Methods of Organic Chemistry), volumes XV/1 and XV/2, and these include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), lysine (Lys), leucine (Leu), methionine (Met), ornithine (Orn), phenylalanine (Phe), proline (Pro), serine (Ser), threonine (Thr), tryptophan (Trp), tyrosine (Tyr) and Valine (Val). Preferred derivatives of α-amino acids are their amides and esters, especially the ($C_1$–$C_6$)-alkyl or benzyl esters of naturally occurring α-amino acids, in which other functional groups can be present, if appropriate protected in a manner known per se. Preferred modified forms of α-amino acids are those in which the carboxyl group has been reduced to —$CH_2OH$. Peptides capable of being derivatized, modified or protected in the manner described above are preferably understood as meaning oligopeptides composed of naturally occurring α-amino acids.

The invention also relates to a process for the preparation of a salt as claimed in one of claims 1 to 9, wherein HOObt and the amino compound are together dissolved in a suitable solvent and the salt is (a) precipitated from this solution by the addition of another solvent in which the salt is less soluble, (b) separated from this solution by concentration or (c) separated from this solution by cooling of the saturated solution.

The salts are preferably prepared in the following manner: The amino compound and the appropriate quantity (1 to 2 equivalents per $NH_2$ group) of HOObt are first dissolved, for example in alcohols, preferably in methanol.

The salts are precipitated from these solutions by the addition of ethers, for example diethyl ether or diisopropyl ether, or the solutions are concentrated and/or cooled and the residue is crystallized from ethers, for example diethyl ether or tert.-butyl methyl ether. In this process, the impurities as a rule remain in the mother liquor. The HOObt content is determined via an NMR spectrum.

The invention further relates to the use of the above-mentioned salts in the purification of amino compounds and in the preparation of carboxamides in the presence of carbodiimides. Like the HOBt salts, the salts can be used directly for acylation, where HOObt has the advantage over HOBt that the racemization is more greatly reduced in the acylation of the bases with peptides (Chem. Ber. 103, 2034–2040 (1970); Chem. Ber. 103, 2024–2033 (1970); K. Brunfeldt (Editor): Peptides 1980, pages 174–179, Scriptor, Copenhagen, 1981; Int. J. Peptide Protein Res. 17, 197–204 (1981)). With active esters of carboxylic acids, for example the 2,4,5-trichlorophenyl esters or the 2- or 4-nitrophenyl esters, the HOObt salts react at a similar rate to the HOBt salts. The acylation with carboxylic acids is generally carried out using carbodiimides. DCC is particularly preferred. The most suitable solvents for the acylation of these salts are strongly polar solvents such as, for example, dimethylformamide or dimethylacetamide. After the reaction, the HOObt can be removed by extraction with $NaHCO_3$ solutions.

The examples which follow serve to illustrate the invention without implying a limitation.

EXAMPLE 1

L-Leucinol.HOObt (H—Leu—ol—HOObt)

11.4 g of LiAlH₄ are added, with stirring, to 250 ml of tetrahydrofuran cooled to —5° C. 28.86 g (0.22 mol) of L-leucine are added to this suspension over a period of 45 minutes, with stirring. The mixture is then boiled under reflux for 4 hours. It is subsequently cooled to 0° C., 250 ml of diethyl ether are added and 50 ml of water are slowly introduced dropwise, with stirring. The precipitate is filtered off with suction and the residue is extracted by boiling with twice 150 ml of methanol and filtered off hot with suction. The combined filtrates are concentrated. The residue is taken up in 100 ml of absolute ethanol, and 200 ml of ether are added. The mixture is left to stand overnight at 4° C., the precipitate is filtered off with suction and the filtrate is concentrated. The resulting oil (26.1 g) is dissolved in 150 ml of methanol. 36 g (0.22 mol) of HOObt and 200 ml of diethyl ether are added and the salt is left to crystallize out at 4° C. The precipitate is filtered off with suction and washed with ether. Yield: 44.5 g of pale yellow crystals (72%), melting point 158°–160° C. (with decomposition), $[\alpha]_D = +6.5°$ (c=1, in methanol).

The following salts were prepared analogously, twice the quantity of HOObt being added in the cases where the amino compounds crystallize with 2 mol of HOObt:

|  | Melting point | $[\alpha]_D$ (c = 1, in methanol) |
| --- | --- | --- |
| H—Thr(Bu$^t$)—ol.2HOObt (from H—Thr(Bu$^t$)—OH) | 147° C. | −8.2° |
| H—Ile—ol.HOObt (from H—Ile—OH) | 178–179° C. | +8.8° |
| H—Thr—ol.2HOObt (from H—Thr—OMe) | 157° C. | −5.7° |
| H—Phe—ol.HOObt (from H—Phe—OH) | 150–152° C. | −0.5° |

EXAMPLE 2

10 mmol of an amino compound and 1.63 g (10 mmol) of HOObt are together dissolved in 20 ml of methanol. 40 ml of diethyl ether are added to this solution. The salt is left to crystallize out at 4° C., filtered off with suction, washed with ether and dried in vacuo.

|  | Melting point | $[\alpha]_D$ (c = 1, methanol) | Yield |
| --- | --- | --- | --- |
| H—Thr—OMe.HOObt | 169–170° C. | −4.7° | 90% |
| H—Ser(Bu$^t$)—OBu$^t$.HOObt | 128° C. | 0° | 85% |

EXAMPLE 3

10.5 ml (100 mmol) of diethylamine are added to a solution of 10 mmol of an Fmoc peptide in 50 ml of dimethylformamide. The mixture is stirred for 5 minutes at room temperature and then concentrated. The residue and 1.65 g (10 mmol) or 3.3 g (20 mmol) of HOObt are together dissolved in 30 ml of methanol. The solution is concentrated and the residue is triturated with ether. The precipitate is filtered off with suction and washed with ether. The HOObt content varies somewhat according to the quantity of HOObt added and the reaction mixture. Although the salts do not crystallize in constant molar ratios, a distinct purification effect is detectable by thin layer chromatography.

|  | Melting point | $[\alpha]_D$ (c = 1, methanol) |
| --- | --- | --- |
| H—Cys(SBu$^t$)—Thr—ol.1.5HOObt | amorphous | −26.3° |
| H—Cys(SBu$^t$)—Leu—ol.HOObt | 155° C. | −45.3° |
| H—Cys(SBu$^t$)—4-Abu—OBu$^t$.2HOObt | 109–111° C. | −5.7° |
| H—Thr—Cys(SBu$^t$)—Thr—ol.1.75HOObt | 140° C. (decomp.) | −55.7° |

EXAMPLE 4

Fmoc—Cys(SBu$^t$)—Thr—ol 12.2 g (20 mmol) of Fmoc—Cys(SBu$^t$)—OTcp are added to a solution of 8.62 g (20 mmol) of H—Thr—ol.2HOObt in 50 ml of dimethylformamide. The mixture is left to stand overnight and concentrated and the residue is partitioned between ethyl acetate and 50 ml of a saturated NaHCO₃ solution. The ethyl acetate phase is then extracted by shaking with a KHSO₄/K₂SO₄ buffer and water, dried over Na₂SO₄ and concentrated. The substance is crystallized from diethyl ether. Yield 70%, melting point 155° C. (decomposition), $[\alpha]_D = −86.5°$ (c=1, methanol).

The following were prepared analogously:

|  | Yield | Melting point | $[\alpha]_D$ (c = 1, methanol) |
| --- | --- | --- | --- |
| Fmoc—Cys(SBu$^t$)—Thr(Bu$^t$)—ol (purification by chromatography on silica gel in methylene chloride) | 75% | amorphous | −69.9° |
| Fmoc—Cys(SBu$^t$)—Leu—ol | 67% | 149° C. (decomp.) | −82.8° |

EXAMPLE 5

Fmoc—Ser(Bu$^t$)—Cys(SBu$^t$)—Leu—ol 1.44 g (7 mmol) of DCC are added at 0° C. to a solution of 2.49 g (6.5 mmol) of Fmoc—Ser(Bu$^t$)—OH and 3.06 g of H—Cys(SBu$^t$)—Leu—ol.HOObt in 25 ml of dimethylacetamide. The mixture is first stirred for 1 hour at 0° C. and then left to stand overnight at room temperature. The precipitate is filtered off with suction and the filtrate is concentrated and worked up as in Example 4.

Yield 3.1 g (71%), melting point 144° C., $[\alpha]_D = −76.6°$ (c=1, methanol).

The following were prepared analogously:

|  | Yield | Melting point | $[\alpha]_D$ (c = 1) |
| --- | --- | --- | --- |
| Fmoc—Thr(Bu$^t$)—Cys(SBu$^t$)—Thr—ol (purification by chromatography on silica gel in methylene chloride/methanol 9.2:0.8) | 72% | amorphous | −46.2° (in methanol) |
| Fmoc—His—Cys(SBu$^t$)—Thr—ol | 80% | 172° C. | −49.2° (in 90% acetic acid) |
| Fmoc—Thr—Cys(SBu$^t$)—Thr—ol | 95% | 175° C. | −90.5° (in methanol) |
| Fmoc—Tyr(Et)—Cys(SBu$^t$)— | 83% | 126° C. | −37.4° |

| | Yield | Melting point | $[\alpha\pi_D(c = 1)$ |
|---|---|---|---|
| | | -continued | |
| Thr—ol | | | (in methanol) |

What is claimed is:

1. A salt of
   (a) 3-hydroxy-4-oxo-3,4-dihydro-1,2,3-benzotriazine and
   (b) a primary monoamino compound containing a primary amino group capable of forming a salt with said 3-hydroxy-4-oxo-3,4-dihydro-1,2,3-benzotriazine, wherein the primary monoamino compound is selected from the group consisting of ($C_1$-$C_6$)-alkyl esters of naturally occurring α-amino acids; ($C_1$-$C_6$)-alkyl esters of 4-amino-butyric acid; naturally occurring α-amino acids and 4-amino-butyric acid in which the carboxyl group has been reduced to —$CH_2OH$; dipeptides and tripeptides consisting of naturally occurring α-amino acids and/or 4-amino-butyric acid bearing a ($C_1$-$C_6$)-alkyl ester function; and dipeptides and tripeptides consisting of naturally occurring α-amino acids and/or 4-aminobutyric acid in which the C-terminal carboxyl group has been reduced to —$CH_2OH$, said naturally occurring α-amino acids being selected from alanine, arginine, asparagine, aspartic acid, cysteine, glutamine, glutamic acid, glycine, histidine, isoleucine, lysine, leucine, methionine, ornithine, phenylalanine, proline, serine, threonine, tryptophan, tyrosine and valine, in which salt the molar ratio 3-hydroxy-4-oxo-3,4-dihydro-1,2,3-benzotriazine: primary monoamino compound is 1:1 to 2:1.

2. The salt as claimed in claim 1 wherein the molar ratio 3-hydroxy-4-oxo-3,4-dihydro-1,2,3-benzotriazine: primary monoamino compound is 1:1.

3. The salt as claimed in claim 1 which is crystalline.

4. The salt as claimed in claim 1 which is amorphous.

5. The salt as claimed in claim 1, wherein the primary monoamino compound is a compound selected from the group consisting of H—Leu—ol, H—Thr—ol, H—Ile—ol, H—Phe—ol and H—Thr($Bu^t$)—ol.

6. The salt as claimed in claim 1, wherein the primary monoamino compound is a compound selected from the group consisting of H—Thr—OMe and H—Ser($Bu^t$)—$OBu^t$.

7. The salt as claimed in claim 1, wherein the primary monoamino compound is a compound selected from the group consisting of H—Cys($SBu^t$)—Thr—ol, H—Cys($SBu^t$)—Leu—ol and H—Thr—Cys($SBu^t$)—Thr—ol.

8. The salt as claimed in claim 1, wherein the primary monoamino compound is H—Cys($SBu^t$)—4—Abu—$OBu^t$.

* * * * *